(12) United States Patent
Leschinsky et al.

(10) Patent No.: US 6,602,270 B2
(45) Date of Patent: Aug. 5, 2003

(54) REDUCED SIZE INTRA-AORTIC BALLOON CATHETER

(75) Inventors: Boris Leschinsky, Waldwick, NJ (US); Robert B. Schock, Sparta, NJ (US)

(73) Assignee: DataScope Investment Corp., Wilmington, DE (US)

( * ) Notice: Subject to any disclaimer, the term of this patent is extended or adjusted under 35 U.S.C. 154(b) by 0 days.

(21) Appl. No.: 09/928,843

(22) Filed: Aug. 13, 2001

(65) Prior Publication Data

US 2003/0032974 A1 Feb. 13, 2003

(51) Int. Cl.⁷ .............................................. A61M 25/10
(52) U.S. Cl. .................. 606/194; 606/191; 604/103.09
(58) Field of Search ................................. 606/194, 195, 606/191; 604/96.01, 103.09, 282

(56) References Cited

U.S. PATENT DOCUMENTS

| | | | | |
|---|---|---|---|---|
| 3,834,394 A | * | 9/1974 | Hunter et al. | 128/325 |
| 4,878,898 A | * | 11/1989 | Griffin et al. | 604/101 |
| 4,901,735 A | * | 2/1990 | von Berg | 128/748 |
| 5,456,665 A | * | 10/1995 | Postell et al. | 604/96 |
| 5,716,373 A | | 2/1998 | Wolvek et al. | |
| 6,190,393 B1 | * | 2/2001 | Bevier et al. | 606/108 |

* cited by examiner

Primary Examiner—Michael J. Milano
Assistant Examiner—Daniel Jacob Davis
(74) Attorney, Agent, or Firm—J. Gary Muhr

(57) ABSTRACT

A reduced size IAB catheter system comprising an IAB catheter disposed within a tube serving both as a insertion sheath and as a reinforcement tube. The tube is preferably disposed about the entire catheter up to the balloon membrane. The catheter remains disposed within the tube during therapy.

29 Claims, 2 Drawing Sheets

REDUCED SIZE INTRA-AORTIC BALLOON CATHETER

BACKGROUND OF THE INVENTION

1. Field of the Invention

The invention relates to a balloon catheter. More particularly, the invention relates to a reduced size intra-aortic balloon catheter and a method for insertion of same.

2. Description of the Prior Art

Intra-aortic balloon (IAB) catheters are used in patients with left heart failure to augment the pumping action of the heart. The catheters, approximately 1 meter long, have an inflatable and deflatable balloon at the inserted distal end. The catheter is typically inserted into the femoral artery over a guidewire and moved up the descending thoracic aorta until the distal tip of the balloon is positioned just below or distal to the left subclavian artery. The proximal end of the catheter remains outside of the patient's body. A gas shuttle passageway for inflating and deflating the balloon extends through the catheter and is connected at its proximal end to an external pump. The patient's central aortic pressure is used to time the balloon and the patient's ECG may be used to trigger balloon inflation in synchronous counterpulsation to the patient's heartbeat.

Intra-aortic balloon therapy increases coronary artery perfusion, decreases the workload of the left ventricle, and allows healing of the injured myocardium. Ideally, the balloon should be inflating immediately after the aortic valve closes and deflating just prior to the onset of systole. When properly coordinated, the inflation of the balloon raises the patient's diastolic pressure, increasing the oxygen supply to the myocardium; and balloon deflation just prior to the onset of systole lowers the patient's diastolic pressure, reducing myocardial oxygen demand.

Intra-aortic balloon (IAB) catheter therapy is the most widely used method of mechanical cardiac assistance. However, limb ischemia remains to be a complication of the IAB therapy accounting up to 10% incidence rate. Historically, IAB catheters have progressed from being quite large in size (12 Fr or 4 mm) down to the recently introduced 8 Fr (2.67 mm) IAB catheter. The unit of Fr is widely used in medical device industry, a diameter of 3 Fr is approximately equal to 1 mm. The advantages of making an IAB catheter smaller are as follows:

- higher blood flow through the limb due to lower restriction from the catheter;
- easier hemostasis after IAB removal due to smaller insertion wound;
- easier insertion of the catheter into tortuous, stenotic, or diseased arterial vessel tree; and
- a lower propensity for kinking.

It is desirable therefore to make an IAB catheter as small as possible without compromising the shuttle gas speed.

Traditionally, IAB catheters have two lumens in the catheter: a gas shuttle lumen and a guidewire lumen. The gas shuttle lumen is substantially fixed in size as it has to be large enough to allow the gas to shuttle back and forth without undue restriction to ensure speedy inflation and deflation of the IAB membrane.

The guidewire lumen serves primarily two functions: to aid in inserting the IAB over a previously placed guidewire, and to monitor blood pressure while the IAB is functioning. Recent discoveries and progress with miniature pressure sensors have made it conceivable to place a small pressure sensor into the tip of the catheter, and to monitor the blood pressure via electrical or fiber optic lines running along the catheter to the outside unit with even greater accuracy and stability then through the guidewire lumen, see U.S. patent application Ser. No. 09/734,755, filed on Dec. 12, 2000, herein incorporated by reference in its entirety. Local telemetry and wireless transmission of blood pressure information from the IAB tip sensor to the outside of the patient is also possible. In any case, the pressure monitoring function of the guidewire lumen may be replaced in the future with a sensor embedded in the IAB tip.

However, insertion of the IAB over a guidewire is still a very desirable feature. Direct attempts to make a smaller IAB catheter without the ability to be inserted over the wire are still in the experimental stage. Therefore, the need exists for a single lumen small profile IAB catheter which is insertable using conventional over-the-guidewire techniques.

Furthermore, the need exists to reduce the size of IAB catheters while maintaining the size of the gas shuttle lumen. IAB catheters are generally designed to be inserted through an introducer sheath. Present day IAB catheters, however, are designed for both types of insertion, through a sheath as well as for optional sheathless insertion. As such, the wall thickness of the catheter and the material chosen have to provide sufficient strength and catheter stiffness to withstand the insertion of the IAB and to support the inflation and deflation of the balloon membrane against the pressures generated by the oncoming waves of blood in the descending aorta. Given the need to maintain the size of the gas shuttle lumen, reduction of the IAB catheter profile becomes a difficult design problem. The present invention involves the use of an extended sheath for use during insertion and pumping which allows for a reduction in the overall size of the IAB catheter while maintaining the size of the gas shuttle lumen.

While the present intra-aortic balloon system may be suitable for the particular purpose employed, or for general use, it is not as suitable for the purposes of the present invention as disclosed hereafter.

SUMMARY OF THE INVENTION

Accordingly, it is an object of the invention to produce an IAB catheter allowing for higher blood flow through the limb due to a lower restriction from the catheter.

It is a further object of the invention to produce an IAB catheter allowing for easier hemostasis after removal due to a smaller insertion wound.

It is another object of the invention to produce an IAB catheter which provides for an easier insertion into tortuous, stenotic, or diseased arterial vessel trees.

It is still another object of the invention to produce an IAB catheter having a smaller propensity for kinking.

The invention is a reduced size IAB catheter system comprising an IAB catheter disposed within a tube serving both as an insertion sheath and as a reinforcement tube. The tube is preferably disposed about the entire catheter up to the balloon membrane. The catheter remains disposed within the tube during therapy.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
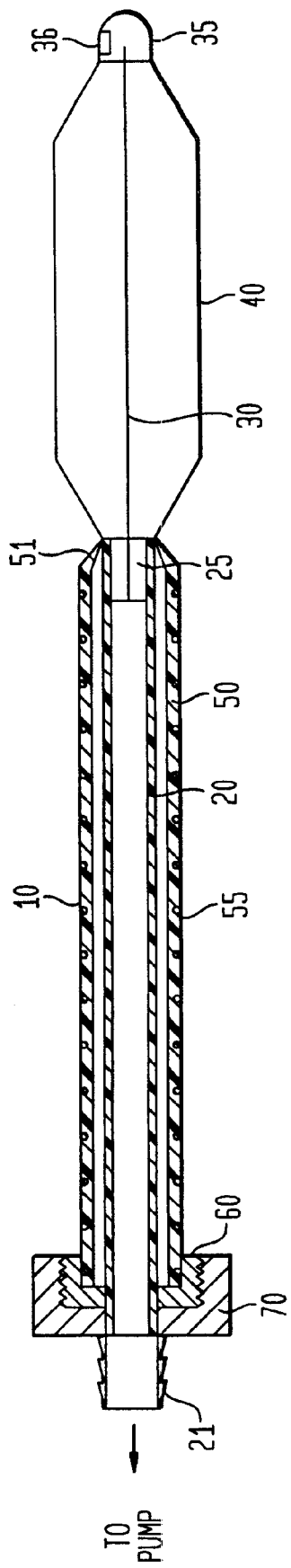
FIG. 1 is a longitudinal cross sectional view of a single lumen intra-aortic balloon catheter system of the present invention including an extended insertion sheath.

FIG 1 illustrates a novel single lumen IAB catheter assembly, generally designated (10), comprising a reinforcement/insertion tube 50, catheter cap 60, tube cap 70, and catheter tube (20) attached at a distal end to a balloon membrane (40) A fitting (25) is disposed within a distal end of catheter tube (20) to enhance the stiffness of the catheter for connection to a proximal end of a stylet wire (30), designed to support balloon membrane (40). Stylet wire (30) may vary in stiffness along its length such that the distal end is more flexible than the proximal end, see U.S. patent application Ser. No. 09/734,755, filed on Dec. 12, 2000, herein incorporated by reference in its entirety. A tip (35) is attached to a distal end of stylet wire (30) and seals off a distal end of balloon membrane (40). Other known single lumen designs can be utilized here as well, including those disclosed in U.S. Pat. No. 5,716,373, issued to Wolvek et al, herein incorporated by reference. One example of an alternate design is to incorporate stylet wire (30) along a portion or even the entire length of catheter (20) 50 that there is no need for fitting (25) Alternatively, a wire reinforced catheter can be used and an exposed distal portion can be used as a stylet, see U.S. patent application Ser. No. 09/734,755, filed on Dec. 12, 2000. The proximal end of the catheter (20) is attached to female tube cap (70) terminating in a connector (21) for connection to an IAB pump (not shown)

A pressure sensor (36) may be optionally incorporated into IAB catheter assembly (10) connected to IAB tip 35 (without size restrictions typically associated with IAB tips designed to accommodate a guidewire lumen) and the signal may be transmitted optically or electronically down the length of the catheter (transmission means not shown), see U.S. patent application Ser. No. 09/734,755, filed on Dec. 12, 2000, herein incorporated by reference in its entirety, and U.S. patent application Ser. No. 09/735,076, filed on Dec. 12, 2000. Alternatively, pressure information may be obtained though other pressure lines placed elsewhere in the patient's body such as a radial line.

Reinforcement/insertion tube (50) is disposed over at least a portion but preferably the entire length of catheter (20) up to the proximal end of balloon membrane (40), as shown in FIG. 1. Tube (50) is connected to male catheter cap (60), which is designed to accept female tube cap (70) either by threads, snap-fit or other known techniques. Note that the cap sexes may be reversed. A distal end of the tube (50) contains a transition end (51) designed in a similar way as the tips of introducer sheaths to envelop the catheter (20). It is highly desirable but not essential to reinforce the wall of at least one component of the IAB assembly (10), in this case the tube (50), with metal wire (55) as shown on the drawings. That will provide for better insertion and prevent kinking of IAB catheter assembly 10. An inner diameter of tube (50) is substantially the same as an outer diameter of catheter tube (20), i.e. they are within 0.003 and 0.005 inches (0.08 and 0.13 mm).

In the preferred embodiment, balloon membrane (40) has a volume of 40 cubic centimeters and is made from polyurethane. Balloon membrane (40) is wrapped around stylet (30) to assure the minimum profile of the system for insertion. The outer diameter of the wrapped balloon membrane (40) is preferably equal to or less than an outer diameter of catheter tube (20), as disclosed in U.S. patent application Ser. No. 09/210,922, filed on Dec. 14, 1998, herein incorporated by reference in its entirety.

Catheter tube (20) is made from either polyurethane, polyimide, or Pebax (a trade mark of Elf Atochem Inc, Birdsboro, Pa.), has an inner diameter of approximately 0.073 inches (1.85 mm) and an outer diameter of approximately 0.086 inches (2.18 mm). Catheter tube (20) has a length between approximately 19 and 25 inches (48.25 and 63.5 cm), preferably approximately 20 inches (50.8 cm). Reinforcement/insertion tube (50) preferably has an inner diameter of approximately 0.089 inches (2.26 mm), an outer diameter of approximately 0.103 inches (2.62 mm), and is preferably made from polyurethane reinforced with metal wire having a diameter of approximately 0.004 inches (0.10 mm). This design is equivalent in its outside diameter to a 6 Fr interventional sheath. The design may be somewhat upsized respectively to be equal to the 7 or 8 Fr sheath if needed. The length of tube (50) should be less than but within approximately four or five inches (10 or 13 cm) of catheter tube (20). Preferably, tube (50) should be approximately the same length as catheter tube (20) or at least long enough (over 15 inches or 38 cm) to assure proper support for catheter tube (20) during pumping.

Note that due to the reduced outer diameter and wall thickness of the catheter of the present invention, catheter tube (20) may not be able to be independently advanced into the blood vessel. Even if a gas lumen insert is used to enhance stiffness during insertion, catheter tube (20) may buckle during therapy. Accordingly, catheter tube (20) is advanced into a patient's blood vessel through tube (50). Furthermore, tube (50) remains disposed about catheter tube (20) during therapy to support the catheter tube (20). As discussed above, tube (50) should be at least long enough to assure proper functioning of catheter tube (20) during pumping.

Use of an outer tube in conjunction with a reduced size IAB is an essential feature of the invention. IAB catheters are often inserted through a sheath which is generally short relative to the catheter, i.e. at least four or five inches shorter than the catheter tube length. The typical sheath is only about 6 inches (15 cm) long and is just long enough to provide access to the blood vessel, typically a femoral artery. The present invention involves reducing the size of the catheter, and thus weakening it, but then making up for this by extending the length of the insertion sheath and leaving the sheath disposed about the catheter during pumping.

IAB catheters on the market typically have a wall thickness in the range of approximately 0.009 to 0.013 inches (0.23 to 0.33 mm) and inner diameters in the range of approximately 0.085 to 0.110 inches (2.16 to 2.79 mm). The wall thickness of catheter (10) is preferably between 0.004 and 0.008 inches (0.10 and 0.20 mm) and the inner diameter is preferably between 0.065 and 0.080 inches (1.65 and 2.03 mm). Note also that typical IAB insertion sheaths have an outer diameter of approximately 0.125 inches to 0.160 inches (3.18 to 4.06 mm). Outer tube (50) of the present invention has an outer diameter of between 0.100 and 0.110 inches (2.54 and 2.79 mm), significantly smaller than prior art IAB insertion sheaths. This reduction in insertion sheath size results in a smaller insertion wound size and allows for improved circulation to the lower extremities of the patient during therapy.

Before insertion, catheter (20) with balloon membrane (40) wrapped about stylet (30) is packaged separately from tube (50). It is desirable to provide a gas lumen insert (not shown) inside both tube (50) (similar in design to a conventional dilator used for introducer sheaths) and catheter (20) to ensure kink-free insertion, see U.S. Patent application Ser. No. 09/813,905, filed on Mar. 21, 2001, herein incorporated by reference in its entirety. First, a standard guidewire is placed into the blood vessel. A dilator disposed within tube (50) is advanced over the guide wire into the blood vessel, not dissimilar to placing a typical introducer sheath. Next, the dilator and the guide wire are removed leaving tube (50) in the blood vessel. Catheter tube (20) is then pushed into tube (50) until caps (70) and (60) meet and are locked in place. Balloon membrane (40) extends just beyond a distal end of tube (50). At that point, therapy can be initiated. Removal of IAB catheter assembly (10) is done as a single unit, the same way as present IABs are removed.

Figure 2:
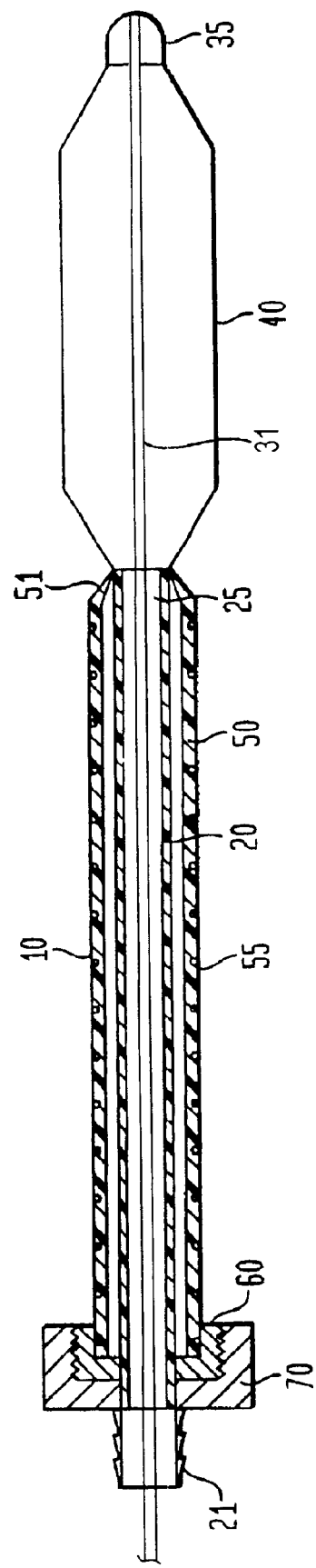
FIG. 2 is a longitudinal cross sectional view of a dual lumen intra-aortic balloon catheter system of the present invention including an extended insertion sheath.

Note that cap (60) may be replaced with a Y-fitting connector which allows for removal of the gas lumen insert through a side branch. Note further that the general concept of the invention, namely using an extended insertion sheath over a reduced sized IAB catheter, as described above, may be applied to other types of IAB catheters, including, but not limited to, co-lumen catheters and dual lumen catheters, see FIG. 2; wherein central tube (31) is disposed within an outer surface of the catheter tube (20) and wherein catheter tube (20) is removably disposed within tube (50). In such case, the IAB catheter may be inserted either over the guide wire lumen or through tube 50, like the single lumen catheter insertion.

As many apparently widely different embodiments of the present invention can be made without departing from the spirit and scope thereof, it is to be understood that the invention is not limited to the specific embodiments thereof except as defined in the appended claims.

What is claimed is:

1. An intra-aortic balloon catheter comprising an inner tube, a tip, and an outer tube, said inner tube being connected on a distal end to a proximal end of a balloon membrane, a distal end of the balloon membrane being connected to the tip, said outer tube being at least partially disposed about the inner tube during inflation and deflation of the balloon membrane and having a length that is shorter but within 4 inches (10 cm) of the length of the inner tube, said inner tube defining a lumen having a valveless communication with an area enveloped by the balloon membrane.

2. The intra-aortic balloon catheter as claimed in claim 1 wherein the inner tube has a thickness between approximately 0.004 inches (0.1 mm) and approximately 0.008 inches (0.2 mm).

3. The intra-aortic balloon catheter as claimed in claim 1 wherein the outer tube and the inner tube are approximately the same length.

4. The intra-aortic balloon catheter as claimed in claim 1 wherein the outer tube is longer than 15 inches (38 cm).

5. The intra-aortic balloon catheter as claimed in claim 1 wherein an inner diameter of said outer tube is larger than but within approximately 0.005 inches (0.18 mm) of an outer diameter of the inner tube.

6. The intra-aortic balloon catheter as claimed in claim 1 further comprising a stylet, a proximal end of the stylet is connected to distal end of the inner tube and a distal end of the stylet is connected to the tip.

7. The intra-aortic balloon catheter as claimed in claim 1 wherein the outer tube is wire reinforced.

8. The intra-aortic balloon catheter as claimed in claim 1 further comprising a pressure sensor connected to the tip.

9. An intra-aortic balloon catheter comprising an inner tube, a tip, and an outer tube, said inner tube being connected on a distal end to a proximal end of a balloon membrane, a distal end of the balloon membrane being connected to a tip, said outer tube being at least partially disposed about the inner tube during inflation and deflation of the balloon membrane and having a length that is shorter but within 4 inches (10 cm) of the length of the inner tube, a proximal end of the inner tube terminates in a connector which is connectable to a connector on a proximal end of the outer tube, a proximal end of the inner tube terminates in a connector which is connectable to a connector on a proximal end of the outer tube.

10. The intra-aortic balloon catheter as claimed in claim 9 wherein the inner tube has a thickness between approximately 0.004 inches (0.1 mm) and approximately 0.008 inches (0.2 mm).

11. The intra-aortic balloon catheter as claimed in claim 9 wherein the second outer tube is longer than 15 inches (38 cm).

12. An intra-aortic balloon catheter comprising an inner tube, a first outer tube, a second outer tube, a balloon membrane, and a tip, a distal end of the first outer tube is connected to a proximal end of the balloon membrane, a distal end of the balloon membrane is connected to the tip, the inner tube is disposed within an outer surface of the first outer tube, the second outer tube being at least partially disposed about the first outer tube during inflation and deflation of the balloon membrane and having a length that is shorter but within 4 inches (10 cm) of the length of the first outer tube.

13. The intra-aortic balloon catheter as claimed in claim 12 wherein the first outer tube and the second outer tube have approximately the same length.

14. The intra-aortic balloon catheter as claimed in claim 12 wherein an inner diameter of said second outer tube is larger than but within approximately 0.005 inches (0.18 mm) of an outer diameter of the first outer tube.

15. The intra-aortic balloon catheter as claimed in claim 12 wherein a proximal end of the first outer tube terminates in a connector which is connectable to a connector a proximal end of second outer tube.

16. The intra-aortic balloon catheter as claimed in claim 12 wherein the first outer tube has a thickness between approximately 0.004 inches (0.1 mm) and approximately 0.008 inches (0.2 mm).

17. The intra-aortic balloon catheter as claimed in claim 12 wherein the second outer tube is longer than 15 inches (38 cm).

18. A method for inserting and operating an intra-aortic balloon catheter comprising an inner tube, a tip, and an outer tube, said inner tube being connected on a distal end to a proximal end of a balloon membrane, a distal end of the balloon membrane being connected to the tip, said method comprising the steps of:

(a) inserting a guide wire into a blood vessel of a patient;

(b) advancing the outer tube over the guide wire into the blood vessel, a proximal portion of the outer tube remaining outside the blood vessel;

(c) removing the guide wire from the blood vessel;

(d) advancing the inner tube through the outer tube such that the balloon membrane projects from a distal end of the outer tube a distance no greater than approximately 4 inches (10 cm), a proximal portion of the inner tube remains outside the blood vessel; and (e) initiating inflation and deflation of the balloon membrane while the outer tube is disposed about the inner tube.

19. The method as claimed in claim 18 wherein the inner tube is advanced onto the outer tube in step (d) such that a distal end of the inner tube is approximately lined up with a distal end of the outer tube.

20. The method as claimed in claim 18 wherein the outer tube is longer than 15 inches (38 cm).

21. The method as claimed in claim 18 wherein the inner tube has a thickness between approximately 0.004 inches (0.1 mm) and approximately 0.008 inches (0.2 mm).

22. The method as claimed in claim 18 wherein the inner tube is advanced into the outer tube in step (d) such that a distal end of the inner tube is approximately lined up with a distal end of the outer tube.

23. The method as claimed in claim 18 wherein the outer tube is longer than 15 inches (38 cm).

24. A method for inserting and operating an intra-aortic balloon catheter comprising an inner tube, a first outer tube, a second outer tube, a tip, and a balloon membrane, the first outer tube being connected on a distal end to a proximal end of a balloon membrane, a distal end of the balloon membrane being connected to the tip, the inner tube being disposed within an outer surface of the first outer tube, said method comprising the steps of:

(a) inserting a guide wire into a blood vessel of a patient;

(b) advancing the second outer tube over the guide wire into the blood vessel, a proximal portion of the second outer tube remaining outside the blood vessel;

(c) removing the guide wire from the blood vessel;

(d) advancing the first outer tube through the second outer tube such that the balloon membrane projects from a distal end of the second outer tube a distance no greater than approximately 4 inches (10 cm), a proximal portion of the first outer tube remains outside the blood vessel; and (e) initiating inflation and deflation of the balloon membrane while the second outer tube is disposed about the first outer tube.

25. The method as claimed in claim 24 further comprising the step of securing the first outer tube to the second outer tube prior to the initiation of inflation and deflation of the balloon membrane.

26. The method as claimed in claim 24 further comprising the preliminary step of dilating the blood vessel.

27. The method as claimed in claim 24 wherein the inner tube has a thickness between approximately 0.004 inches (0.1 mm) and approximately 0.008 inches (0.2 mm).

28. The method as claimed in claim 24 wherein the first outer tube is advanced into the second outer tube in step (d) such that a distal end of the first outer tube is approximately lined up with a distal end of the second outer tube.

29. The method as claimed in claim 24 wherein the outer tube is longer than 15 inches (38 cm).

* * * * *